(12) United States Patent
Dooley et al.

(10) Patent No.: US 8,216,396 B2
(45) Date of Patent: *Jul. 10, 2012

(54) SHAPE MEMORY ALLOY ARTICLES WITH IMPROVED FATIGUE PERFORMANCE AND METHODS THEREFOR

(75) Inventors: Bret A. Dooley, Flagstaff, AZ (US); Christopher C. Lasley, Flagstaff, AZ (US); Michael R. Mitchell, Flagstaff, AZ (US); Robert R. Steele, Flagstaff, AZ (US); Eric M. Tittelbaugh, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/873,191

(22) Filed: Aug. 31, 2010

(65) Prior Publication Data
US 2010/0331946 A1  Dec. 30, 2010

Related U.S. Application Data

(63) Continuation of application No. 10/428,872, filed on May 2, 2003, now Pat. No. 7,789,979.

(51) Int. Cl.
*A61F 2/82* (2006.01)
*C22C 19/03* (2006.01)
(52) U.S. Cl. ........................ 148/402; 623/1.13; 623/1.19
(58) Field of Classification Search .................. 148/402
See application file for complete search history.

(56) References Cited

U.S. PATENT DOCUMENTS 3,948,688 A    4/1976  Clark
4,067,752 A    1/1978  Brook et al.
4,205,293 A    5/1980  Melton et al.
4,631,094 A    12/1986 Simpson et al.
(Continued)

FOREIGN PATENT DOCUMENTS

EA          95/31945 A1      5/1995
(Continued)

OTHER PUBLICATIONS

Abstracts from the 2003 International Conference on Shape Memory and Superelastic Technologies. Posted Jan. 27, 2003 at <http//www.smst.org/smst2003abstracts.pdf.> p. 7 of 42.

(Continued)

*Primary Examiner* — George Wyszomierski
(74) *Attorney, Agent, or Firm* — Wayne D. House

(57) ABSTRACT

Articles made of shape memory alloys having improved fatigue performance and to methods of treating articles formed from shape memory alloy materials by pre-straining the articles (or desired portions of the articles) in a controlled manner so that the resultant articles exhibit improved fatigue performance. The shape memory articles are preferably medical devices, more preferably implantable medical devices. They are most preferably devices of nitinol shape memory alloy, most particularly that is superelastic at normal body temperature. The pre-straining method of the present invention as performed on such articles includes the controlled introduction of non-recoverable tensile strains greater than about 0.20% at the surface of a desired portion of a shape memory alloy article. Controlled pre-straining operations are performed on the shape-set nitinol metal to achieve non-recoverable tensile strain greater than about 0.20% at or near the surface of selected regions in the nitinol metal article. The pre-straining operations result in a significant increase in fatigue life of the selectively treated regions and an overall improvement in the fatigue performance of the device.

6 Claims, 9 Drawing Sheets

U.S. PATENT DOCUMENTS

| | | | |
|---|---|---|---|
| 4,665,906 | A | 5/1987 | Jervis |
| 4,830,262 | A | 5/1989 | Ishibe |
| 4,919,177 | A | 4/1990 | Homma |
| 4,935,068 | A | 6/1990 | Duerig |
| 5,069,226 | A | 12/1991 | Yamauchi et al. |
| 5,190,718 | A | 3/1993 | Buffard et al. |
| 5,490,859 | A | 2/1996 | Mische et al. |
| 5,611,874 | A | 3/1997 | Zadno-Azizi et al. |
| 5,628,787 | A | 5/1997 | Mayer |
| 5,782,741 | A | 7/1998 | Bradshaw et al. |
| 5,836,066 | A | 11/1998 | Ingram |
| 5,842,312 | A | 12/1998 | Krumme et al. |
| 5,843,244 | A | 12/1998 | Pelton et al. |
| 6,019,779 | A | 2/2000 | Thorud et al. |
| 6,053,992 | A | 4/2000 | Wu et al. |
| 6,068,623 | A * | 5/2000 | Zadno-Azizi et al. ........ 604/530 |
| 6,165,140 | A | 12/2000 | Ferrera |
| 6,165,210 | A | 12/2000 | Lau et al. |
| 6,214,016 | B1 | 4/2001 | Williams et al. |
| 6,579,246 | B2 * | 6/2003 | Jacobsen et al. ............. 600/585 |
| 6,981,982 | B2 | 1/2006 | Armstrong et al. |
| 7,022,063 | B2 | 4/2006 | Lau et al. |
| 7,731,744 | B1 * | 6/2010 | Cox ............................ 623/1.14 |
| 7,789,979 | B2 | 9/2010 | Dooley et al. |
| 7,811,393 | B2 * | 10/2010 | Dooley et al. ................. 148/402 |
| 2002/0052627 | A1 | 5/2002 | Boylan et al. |
| 2003/0045786 | A1 | 3/2003 | Zhao |
| 2003/0060873 | A1 | 3/2003 | Gertner et al. |

FOREIGN PATENT DOCUMENTS

| | | |
|---|---|---|
| EP | 812928 | 12/1997 |
| EP | 1170393 | 1/2002 |
| WO | 93/19804 | 10/1993 |
| WO | 97/49353 | 12/1997 |
| WO | 00/50100 | 8/2000 |
| WO | 01/95697 | 12/2001 |
| WO | 02/36841 | 5/2002 |
| WO | 03/002037 | 1/2003 |
| WO | 03/002166 | 1/2003 |

OTHER PUBLICATIONS

Duerig TW, Pelton AR, Nitinol Development Corporation Ti-Ni Shape Memory Alloys. Materials Properties Handbook: Titanium Alloys 1994; p. 1035-1048.

Duerig TW, Pelton AR, Stockel D Superelastic Nitinol for Medical Devices. Medical Plastics and Biomaterials Mar./Apr. 1997; p. 30-43.

Eucken S, Duerig TW The Effects of Pseudoelastic Prestraining on the Tensile Behaviour and Two-Way Shape Memory Effect in Aged NiTi. Acta Metall 1989; v37, n8:2245-2252.

Harrison WJ and Lin ZC. The Study of Nitinol Bending Fatigue. Proceedings of the International Conference on Shape Memory and Superelastic Technologies Apr.-May 2000, p. 391-396.

Hodgson DE. Shape Memory Alloys. In: ASM Handbook, vol. 2. ASM International 1990; 897-902.

Kim YS and Miyazaki S. Fatigue Properties of Ti-50.9 at % Ni Shape Memory Wires. Proceedings of the Second International Conference on Shape Memory and Superelastic Technologies, Mar. 1997, p. 473-478.

Kugler C et al. Non-Zero Mean Fatigue Test Protocol for NiTi. Proceedings of the International Conference on Shape Memory and Superelastic Technologies Apr.-May 2000, p. 409-417.

Lin ZC and Boylan J. The Effect of Cold-Work Texture On The Superelastic Characteristics of Nitinol Sheet. Materials Science Forum 2002; 394-395:313- 316.

Martynov V and Basin F. Effect of Constraining Temperature On The Postdeployment Parameters of Self-Expanding Nitinol Stents. Proceedings of the International Conference on Shape Memory and Superelastic Technologies Apr.-May 2000, p. 649-655.

McKelvey AL and Ritchie RO. Fatigue-Crack Propagation in Nitinol, A Shape-Memory and Superelastic Endovascular Stent Material. J Biomed Mater Res, 1999; 47:301-308.

Melton KN, Raychem Corporation Ni-Ti Based Shape Memory Alloys. In: Engineering Aspects of Shape Memory Alloys, ed. Duering TW, Melton KN, Stockel D, Wayman CM. Butterworth-Heinemann 1990; 21-35.

Miyazaki S Thermal and Stress Cycling Effects and Fatigue Properties of Ni-Ti Alloys. In: *Engineering Aspects of Shape Memory Alloys*, ed. Duerig TW, Melton KN, Stockel D, Wayman CM. London: Butterworth-Heinemann; 395-413, 1990.

Morgan NB, Painter J, Moffat A. Mean Strain Effects and Microstructural Observations During In-Vitro Fatigue Testing of NiTi. Presented at the International Conference on Shape Memory and Superelastic Technologies May 5, 2003.

Poncet PP. Nitinol Medical Device Design Considerations. Proceedings of the International Conference on Shape Memory and Superelastic Technologies Apr.-May 2000, p. 441-455.

Porter GA et al. Fatigue and Fracture Behavior of Nickel-Titanium Shape-Memory Alloy Reinforced Aluminum Composites. Materials Science and Engineering 2001; A314:186-193.

Tolomeo D et al. Cyclic Properties of Superelastic Nitinol: Design Implications. Proceedings of the International Conference on Shape Memory and Superelastic Technologies Apr.-May 2000, p. 471-476.

Yang J Fatigue Characterization of Superelastic Nitinol. Proceedings of the Second International Conference on Shape Memory and Superelastic Technologies, Mar. 1997, p. 479-484.

Pelton A et al. Optimization of Processing and Properties of Medical-Grade Nitinol Wire. SMT 2000 Dec. 31, 2000, 361-374.

\* cited by examiner

US 8,216,396 B2

SHAPE MEMORY ALLOY ARTICLES WITH IMPROVED FATIGUE PERFORMANCE AND METHODS THEREFOR

CROSS REFERENCE TO RELATED APPLICATIONS

The present application is a continuation of U.S. application Ser. No. 10/428,872, filed May 2, 2003, now U.S. Pat. No. 7,789,979.

FIELD OF THE INVENTION

The present invention relates to the field of shape memory alloys, medical articles made from shape memory alloys and more specifically to shape memory alloy articles having improved fatigue resistance, and methods of making such articles.

BACKGROUND OF THE INVENTION

Shape memory alloys have been used for a variety of applications since the discovery of shape memory transformation by Chang and Reed in 1932. Nitinol, the near-equiatomic alloy of nickel and titanium (optionally containing ternary, quaternary or more elements such as copper, chromium, iron, vanadium, cobalt or niobium) that thus far offers the most useful shape memory and superelastic properties, was discovered by Buehler and his colleagues in 1962.

Nitinol has proven to be adequately biocompatible for a variety of medical device applications, including implantable applications. It has been used for orthodontics, in a variety of orthopedic devices, for filter devices in various body conduits and for stent devices for maintaining patency of various body conduits, particularly those of the vasculature. These stent devices (including stent-grafts, i.e., stents provided with a flexible covering of a vascular graft material such as porous expanded polytetrafluoroethylene) are generally inserted into a body conduit at a site remote from the intended implantation location, and transported to the desired location by a catheter or similar device. They are usually inserted in a collapsed or compacted state to enable their movement through the body conduit to the desired implantation site, at which location they are expanded to the desired size to interferably fit within the conduit and hold the conduit open at that location. While these devices are most often used for cardiac applications, they are also used for the repair of thoracic and abdominal aortic aneurysms and for peripheral and carotid applications.

Many of these stent devices are made from materials intended to be expanded by the application of a force applied internal to the tubular device, usually by the inflation of a catheter balloon on which the device was mounted for insertion into the body conduit. These balloon-expandable devices are most often made from a plastically deformable material such as a stainless steel. Many other stents are made from shape memory materials, particularly nitinol, and take advantage of the shape memory or superelastic properties so that they may be implanted simply by releasing the constrained, compacted device and allowing it to self-expand at the desired implantation site.

Stent devices should be adequately flexible to enable them to be delivered through bends in the sometimes-tortuous pathways of a body conduit. They may also need to be adequately flexible to conform to bends in the body conduit at the implantation site, and to be able to accommodate movement of the body conduit. This is particularly true in the vasculature, where a vessel often changes dimension as a function of systole and diastole. These devices consequently should also have good fatigue resistance.

Shape memory materials can exhibit pseudoelastic (superelastic) behavior, allowing the material to recover a significant amount of strain due to the reversible, isothermal metallurgical phase transformations by changes in the state of stress. The superelastic behavior is characterized by a linear elastic and a nonlinear pseudoelastic stress-strain response allowing the material to recover a significant amount of strain due to the reversible austenitic-martensitic phase transformation. Conventional nitinol materials can typically recover principle strains on the order of up to 8% (see "Nitinol Medical Device Design Considerations" by Philippe P. Poncet, SMST-2000: Proceedings of the International Conference on Shape Memory and Superelastic Technologies, pp. 441-455). The superelastic behavior of nitinol allows for the design of devices that exert a relatively constant stress over a wide range of strains or shapes. This unique behavior has been utilized in the design of many implantable medical devices such as stents and stent-grafts.

The phase stability of nitinol is a function of both temperature and stress. The phase stability in the unstressed state is characterized by the transformation temperatures $M_f$, $M_s$, $A_s$, and $A_f$. Martensite is the stable phase at temperatures below $M_f$, the martensitic finish temperature. Upon heating, the martensitic structure begins a reversible thermoelastic phase transformation to austenite when the temperature reaches $A_s$, the austenitic start temperature. The transformation to austenite is completed when the temperature reaches $A_f$, the austenitic finish temperature. Upon cooling the austenite, the material begins to transform to martensite at a temperature equal to $M_s$, the martensitic start temperature, and completes its transformation to martensite at a temperature equal to $M_f$, the martensitic finish temperature.

The shape memory effect of nitinol is demonstrated by shaping the material in the relatively high-temperature austenitic phase and setting the shape by an appropriate heat treatment. Upon cooling the material below the martensitic transformation temperature, the material can be deformed to a second shape configuration while in the martensitic state. Upon heating to temperatures above the austenitic transformation temperature the material will return to its original shape configuration. Conventional nitinol materials can typically recover up to 8% strain by this shape memory effect (reference ASM Handbook, Volume 2, Shape Memory Alloys, Darel Hodgson et al., page 899).

The superelastic effect of nitinol is demonstrated by the application of stress to the nitinol material at temperatures above the austenitic transformation temperature, and below $M_d$, the maximum temperature at which stress-induced martensite can be formed. The initial application of stress in this case causes the austenitic structure to deform in the classical Hookean linear elastic manner until a critical stress is achieved. The application of stress beyond this critical stress results in a nonlinear stress-strain response due to the isothermal reversible transformation to martensite. Upon removal of the applied stress, the material can reversibly transform back to austenite, returning to its original shape. As noted previously, conventional nitinol materials can recover approximately 6-8% strain by this superelastic effect.

The alternating in-vivo load conditions (due to changes such as between systole and diastole) often limit the design of medical devices such as stents and stent-grafts due to the fatigue capability of nitinol materials. Improvements in the fatigue performance of nitinol are desirable to provide an increased fatigue life and fatigue life safety factor and to increase design flexibility for implantable medical devices that include nitinol.

Various publications describe the fatigue resistance of devices made from shape memory materials. European Patent Application EP1170393 describes a method for improving fatigue performance of actuators made from materials that have shape memory effect. The process includes introducing significant cold work, applying stress in the expected loading direction, and heating above the recrystallization temperature for short times to create a uniform, fine-grained, microstructure.

According to a published article, "Cyclic Properties of Superelastic Nitinol: Design Implications" (SMST-2000: Proceedings of the International Conference on Shape Memory and Superelastic Technologies, D. Tolomeo, S. Davidson, and M. Santinoranont, pp. 471-476) strain-controlled fatigue tests were conducted with various pre-strain conditions up to 6% pre-strain. Samples were subjected to strains up to 6%, then unloaded to a specified cyclic displacement. The endurance limits for different pre-strain values remained relatively constant.

A published article titled "Effect of Constraining Temperature on the Postdeployment Parameters of Self-Expanding Nitinol Stents" (SMST-2000: Proceedings of the International Conference on Shape Memory and Superelastic Technologies, Martynov and Basin, pp. 649-655) describes the evaluation of retaining temperature on the post deployment parameters of 28 mm aortic-size stents having a typical diamond shaped stent cell structure. The article states that "The maximum deformation of any stent element in the fully compressed state (when the stent is packed into a delivery catheter) should not exceed the available reversible deformation limit, which is about 6 to 8%, depending on the material used."

In another published article, "Fatigue and Fracture Behavior of Nickel-Titanium Shape Memory Alloy Reinforced Aluminum Composites," authors Porter and Liaw describe an aluminum matrix composite reinforced with discontinuous nitinol particulates by powder metallurgy processing. The reinforced composite material is cold rolled at minus thirty degrees centigrade (−30° C.). Upon re-heating, the nitinol transforms to austenite creating residual internal stresses around each particle to strengthen the material. Improved fatigue life was observed compared to the unreinforced control matrix material.

An article entitled "The Study of Nitinol Bending Fatigue" (W. J. Harrison and Z. C. Lin, SMST-2000, Proceedings of the International Conference on Shape Memory and Superelastic Technologies) describes fatigue testing of nitinol samples subjected to alternating strain to simulate the effects of changing strain resulting from systole and diastole, and optionally subjected to an additional constant strain (mean strain) that would be expected to result from the interference between an expanded stent and the vessel into which it has been fitted. The samples tested were cut from nitinol tubing. The samples showed good fatigue life, with the fatigue life being greater for samples exposed to higher mean strain. This result suggests that that the samples had apparently been cut at their small diameter (i.e., the "compacted" diameter appropriate for insertion of such a device into a body conduit) and subsequently expanded to a larger diameter at which they were tested, as opposed to having been cut at the larger, expanded diameter and then compressed slightly to create the mean strain.

SUMMARY OF THE INVENTION

The present invention relates to articles made of shape memory alloys having improved fatigue performance and to methods of treating articles formed from shape memory alloy materials by pre-straining the articles (or desired portions of the articles) in a controlled manner so that the resultant articles exhibit improved fatigue performance.

The shape memory articles are preferably medical devices, more preferably implantable medical devices. They are most preferably devices of nitinol shape memory alloy, most particularly that is superelastic at normal body temperature (approximately 37° C.).

Implantable medical devices are those devices that are intended to remain within a living body for periods of 24 hours or longer.

The shape memory alloy articles may be produced from materials of various shapes, such as wire of various transverse cross sectional shapes including circular, elliptical, square, rectangular, etc. Alternatively, the articles may be made by machining precursor forms such as sheets, tubes or rods, as by electrical discharge machining (EDM), laser cutting, chemical milling, or the like.

The pre-straining method of the present invention as performed on such articles includes the controlled introduction of non-recoverable tensile strains greater than about 0.20% at the surface of a desired portion of a shape memory alloy article. Controlled pre-straining operations of the shape-set nitinol metal are performed to achieve non-recoverable tensile strain greater than about 0.20% at or near the surface of selected regions in the nitinol metal article. The pre-straining operations result in a significant increase in fatigue life of the selectively treated regions and an overall improvement in the fatigue performance of the device. The pre-straining treatments described in this invention are useful for increasing the fatigue life safety factor of current nitinol-based medical devices and for incorporating into the design of future implantable medical devices that include nitinol, thereby providing additional design flexibility.

Controlling the amount of pre-strain involves pre-straining the shape memory metal by the controlled application of bending, torsional or a combination of these and/or other forces at pre-determined temperatures. These amounts of pre-strain (resulting in at least about 0.20% non-recoverable strain) may be calculated by analytical methods such as finite element analysis or the like, in conjunction with the material's loading and unloading behavior.

Non-recoverable tensile strain is intended to mean the permanent set, i.e., the plastic deformation that remains upon releasing the tensile pre-strain or stress, arising from the displacement of atoms to new lattice sites, as determined by representative material stress-strain (loading and unloading) behavioral properties, or as measured by techniques such as microhardness testing, x-ray diffraction, backscatter electron Kikuchi patterns, synchrotron radiation, convergent beam electron diffraction or the like.

The method of this invention involves pre-straining articles such that targeted surface regions are subjected to tensile pre-strains exceeding the recoverable strain limit of the material (typically 6%-8% strain), while maintaining a significant portion of the subsurface area (less affected by the pre-strain) within the superelastic material limit. Tensile pre-strains of this type may be induced by the application of forces such as bending or torsional forces. Upon removing the pre-straining force, the lesser-affected superelastic subsurface region of the article allows the bulk article to recover a significant level of strain, such that the article, following the removal of the pre-straining force, returns to or near to its original geometry.

This process thus results in desired local surface regions of the pre-strained article being in a state of compression. A residual compressive stress state has thus been induced at the targeted surface region. The result is a significant improvement in fatigue performance of targeted regions of the article subjected to this pre-straining operation due to the introduction of residual compressive surface stresses.

The process of inducing compressive residual surface stresses at desired locations by the controlled pre-straining operation of the present invention, may also produce a concomitant surface region which is subjected to compression, on the side of the article opposite the targeted region subjected to tension during the pre-straining operation. The compressive strains introduced on the regions opposite the targeted regions may also exceed the recoverable strain limit of the material, resulting in a residual state of tension at these regions upon removal of the pre-straining load. The end result of the pre-straining operation disclosed in this invention is the improvement in fatigue performance at the targeted regions of the medical article, thus resulting in a more fatigue resistant device. This operation can thus be applied to specifically chosen regions of a medical device where service fatigue loading is most severe and improved fatigue performance is desired, or over the entire surface region of the article.

DETAILED DESCRIPTION OF THE INVENTION

The present invention relates to methods of treating implantable medical device components formed from nitinol materials (such as nitinol wire) so that the resultant device exhibits improved fatigue performance. This invention identifies methods to induce non-recoverable tensile strain greater than about 0.20% strain at or near the surface of selected regions of the nitinol metal by controlled pre-straining processes. The non-recoverable tensile strain may thus be greater than about 0.25%, 0.3%, 0.35%, 0.4%, 0.45%, 0.5%, 0.6%, 0.7%, 0.8%, 1.0%, 1.25%, 1.5%, and 2.0%.

Implantable medical devices are typically designed such that the maximum deformation of any portion of the nitinol material does not exceed the available reversible deformation limit, typically 6% to 8% strain, after the shape setting treatments ("Effect of Constraining Temperature on the Postdeployment Parameters of Self-Expanding Nitinol Stents," SMST-2000: Proceedings of the International Conference on Shape Memory and Superelastic Technologies, Martynov and Basin). The purpose of maintaining maximum principle strains below the reversible deformation limit after the shape setting process has been completed is to ensure that the device will preserve its original shape.

The reversible deformation limit is defined as the maximum strain a material can undergo without inducing non-recoverable strain (i.e., permanent set) greater than about 0.20%.

The methods of this invention involve the controlled pre-straining of desired portions of nitinol articles such that targeted surface regions are subjected to tensile strains exceeding the about 0.20% recoverable strain limit of the material, while maintaining a significant portion of the cross-section within the superelastic material limit. Upon removing the pre-straining force, the superelastic region of the structure allows the bulk structure to recover significant levels of strain such that the structure returns to, or near to, its original geometry. This process thus results in desired regions of the pre-strained material that had been subjected to tensile strains beyond their recoverable limit to be in a state of compression. A residual compressive stress state has thus been induced at the targeted surface regions. This process results in a significant improvement in fatigue performance of targeted regions of the structure subjected to this pre-straining operation due to the introduction of residual compressive surface stresses. The controlled process of pre-straining can be accomplished by flexural loading, torsional loading, or any combination of loading conditions designed to induce non-recoverable tensile strains greater than about 0.20% at or near the surface of fatigue-critical locations of a shape-set, nitinol containing implantable medical device.

Figure 1A:
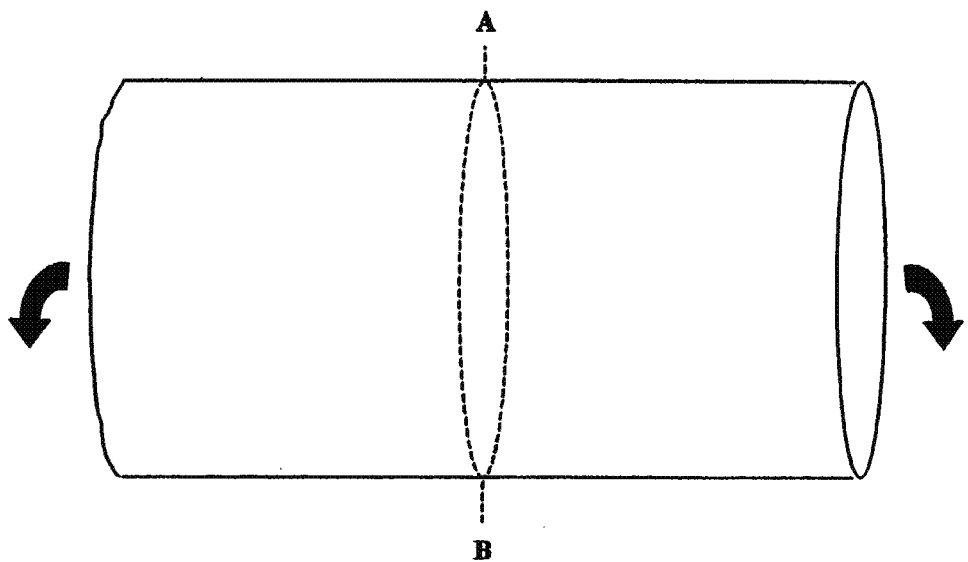
FIG. 1A shows a perspective side view of a nitinol alloy wire of circular cross-section subjected to a pre-straining operation by a controlled bending operation.
Figure 1B:
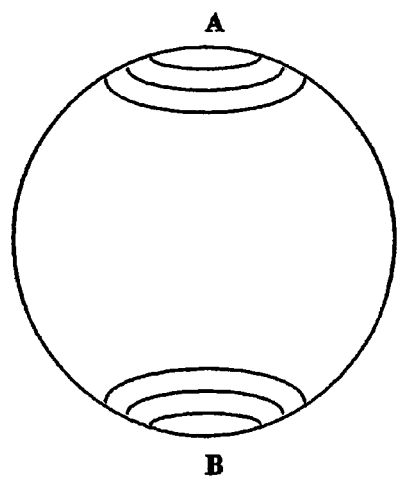
FIG. 1B shows a transverse cross-sectional view taken through the wire of FIG. 1A indicating representative strain contours for the selectively treated cross-sectional area of the wire.

An example of a pre-straining method included as an embodiment of this invention is illustrated in FIGS. 1A and 1B. FIG. 1A shows a nitinol wire of circular cross-section being deformed by a controlled bending pre-straining operation, indicated by the arrows. The transverse cross-section of FIG. 1B shows constant strain contours of the indicated cross-section of the wire during the pre-straining, bending operation in accordance with FIG. 1A, with the region showing arcuate iso-strain contours near location A representing the region subjected to non-recoverable tensile strains greater than about 0.20%. In FIG. 1B, the region showing the iso-strain contours near location B is subjected to compressive strains. Upon removal of the pre-straining force, the superelastic nature of the bulk material (i.e., generally the material outside of the regions indicated by the iso-strain contours) forces the material to return to, or near to, its original shape. This operation thus induces residual compressive stresses at or near the surface location A and residual tensile stresses at or near the surface location B. The result of this pre-straining operation is an improvement in the fatigue performance of the treated region A. This pre-straining method may thus be applied in a controlled manner to treat desired fatigue-critical locations of a device.

Figure 1C:
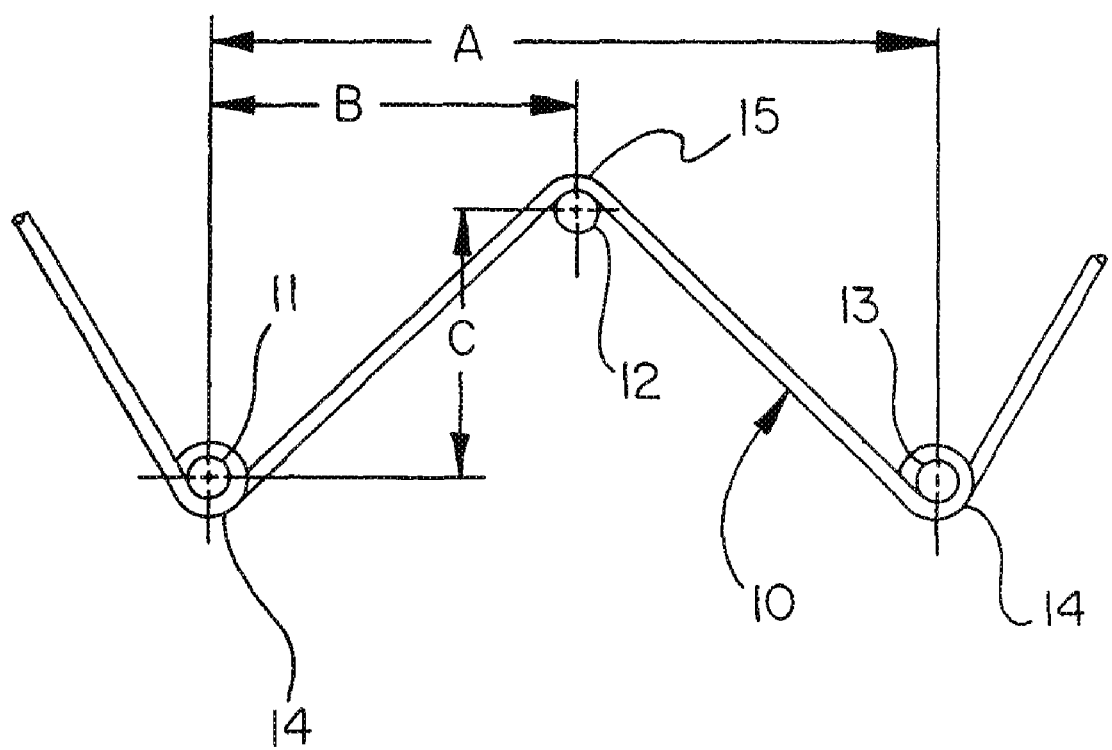
FIG. 1C shows a view of a shape-set nitinol wire specimen: test specimens are pre-strained following the shape-set heat treatment, while control specimens are not.

FIG. 1C shows a view of a shape-set nitinol wire specimen. Wire specimen 10 is formed around pins 11, 12, and 13 and includes about 1.25 turns of the wire around each of pins 11 and 13 as shown, to create loops 14. The two opposing loops (14) are wound in opposite directions (i.e., clockwise and counter-clockwise). The distance between pins 11 and 12 is defined as dimension "A" with dimension "B" (partially defining the location of pin 12, parallel to dimension "A") being half of dimension "A". Dimension "C" finally defines the location of pin 12 as the distance pin 12 is located above a line between pins 11 and 13. Pins 11 and 13 are of equal diameter. The diameter of pin 12 is chosen to provide the desired radius at the apex 15 of the wire specimen. After being formed as shown, these wire specimens 10 are subjected to shape-set heat treatment prior to fatigue testing. Test specimens are pre-strained following the shape-set heat treatment, while control specimens are not.

Figure 2:
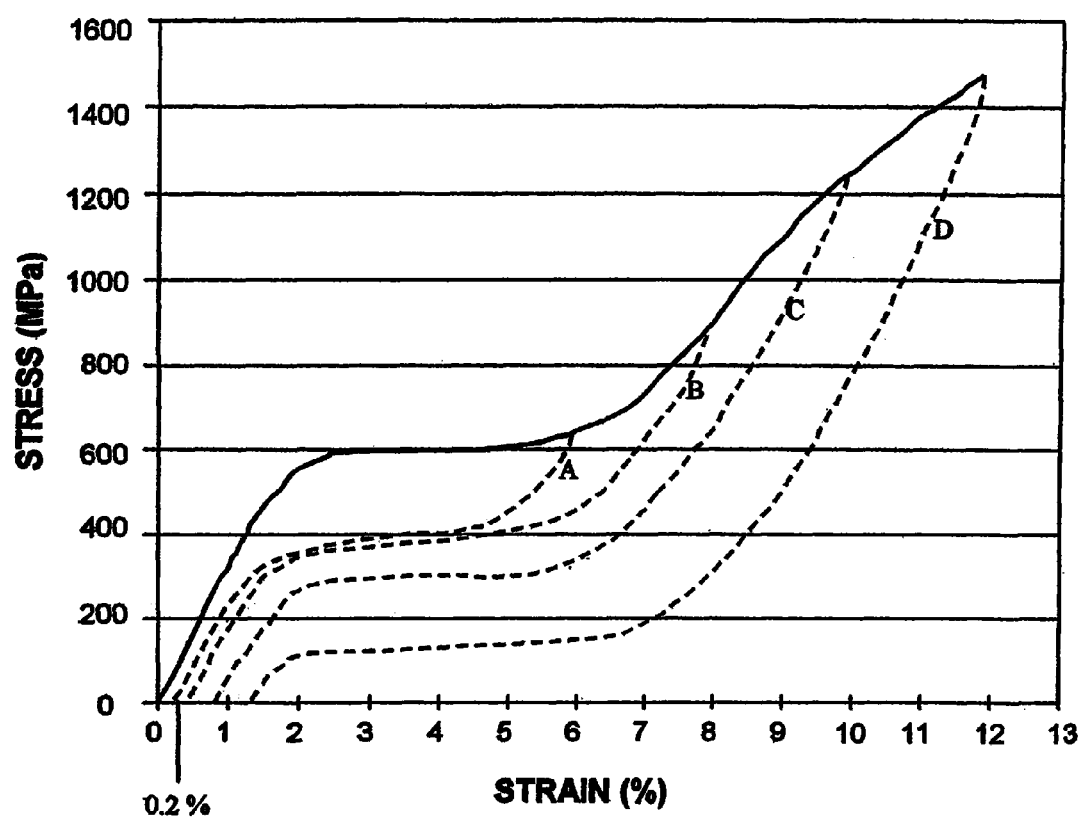
FIG. 2 shows stress-strain curves for nitinol wires subjected to pre-straining that results in non-recoverable tensile strain of less than about 0.20% and for inventive wires subjected to tensile pre-straining at 37° C. that results in non-recoverable tensile strain of greater than about 0.20%.

FIG. 2 shows stress-strain curves for nitinol wire samples loaded at 37° C. in tension, followed by unloading at 37° C., from various pre-strain levels. It is noted that the particular stress-strain response is dependent upon such factors as alloy composition and thermal and mechanical process histories. The resultant non-recoverable tensile strain (i.e., permanent set) increases with increasing pre-strain level. Information obtained from this type of family of stress-strain curves, in conjunction with analytical procedures such as finite element analysis, can be utilized to develop an appropriate temperature, controlled pre-straining (bending) process. This process is designed to induce non-recoverable tensile strain levels greater than about 0.20% at desired, fatigue-critical surface locations of a shape-set nitinol structure. It is apparent this process can be developed for other temperatures as well.

Figure 3:
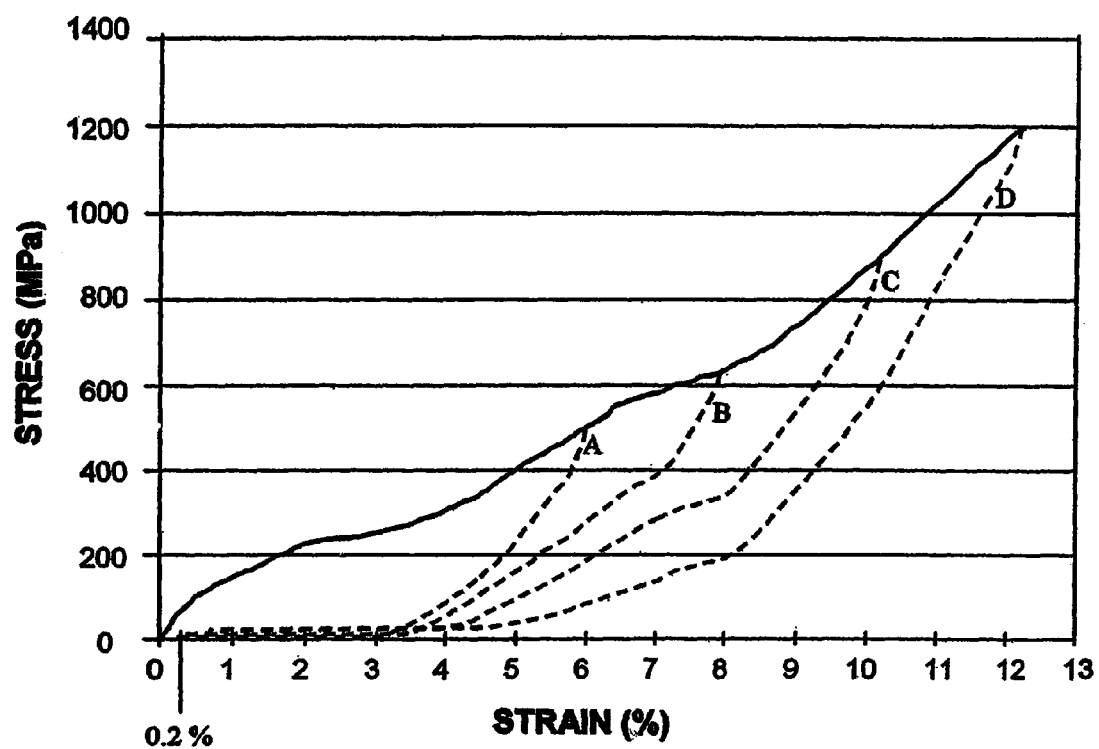
FIG. 3 shows stress-strain curves for nitinol wires subjected to pre-straining that results in non-recoverable tensile strain of less than about 0.20% and for inventive wires that results in non-recoverable tensile strain of greater than about 0.20%, loaded at −30° C. in tension followed by unloading at −30° C. from various pre-strain levels, and heated in the stress-free state to 37° C.

FIG. 3 shows a representative family of stress-strain curves for nitinol wire samples which have been loaded at −30° C. in tension, followed by unloading at −30° C. from various pre-strain levels, and heated in the stress-free state to 37° C. The resultant non-recoverable tensile strain increases with increasing pre-strain level. This family of stress-strain curves, in conjunction with analytical procedures such as finite element analysis, can similarly be utilized to develop an appropriate temperature, controlled pre-straining process designed to induce non-recoverable tensile strain levels greater than about 0.20% at fatigue-critical surface locations of a shape-set nitinol structure.

Figure 4:
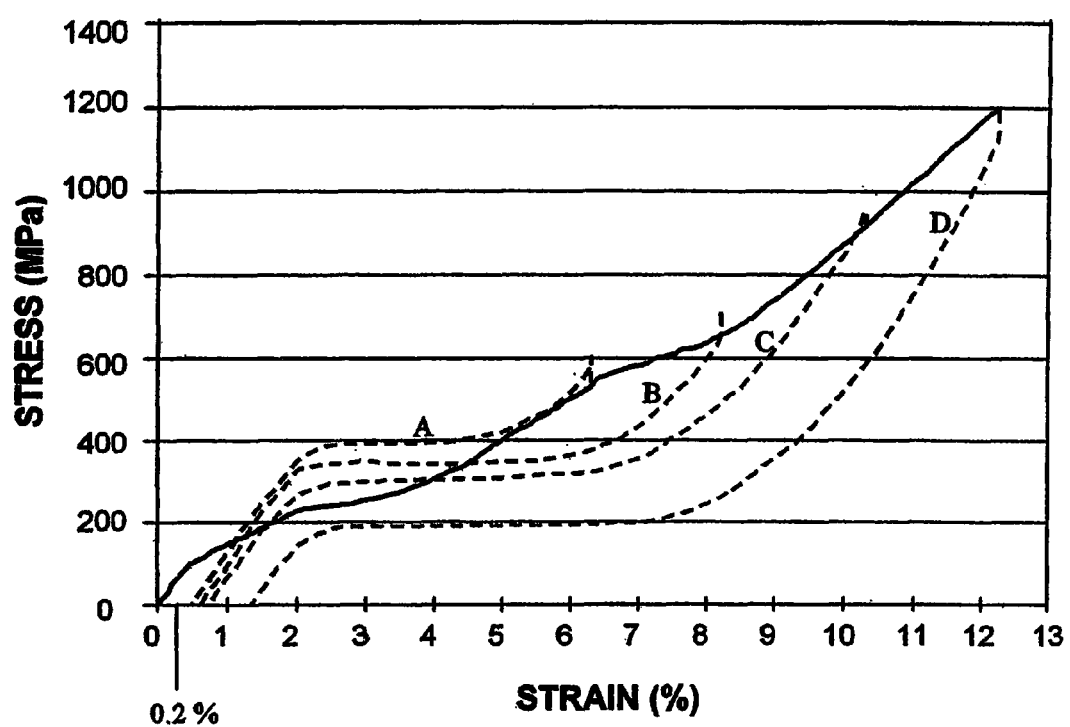
FIG. 4 shows stress-strain curves for nitinol wires loaded at −30° C. in tension, heated to 37° C. while maintained at various pre-strain levels, followed by unloading at 37° C. from the various pre-strain levels.

FIG. 4 shows another representative family of stress-strain curves for nitinol wire samples loaded to various pre-strain levels at −30° C. in tension, heated to 37° C. while maintained at their respective pre-strain condition, followed by unloading at 37° C. from their respective pre-strain condition. The resultant non-recoverable tensile strain increases with increasing pre-strain level. This family of stress-strain curves, in conjunction with analytical procedures such as finite element analysis, can similarly be utilized to develop an appropriate temperature, controlled pre-straining process designed to induce non-recoverable tensile strain levels greater than about 0.20% at fatigue-critical surface locations of a shape-set nitinol structure.

Figure 5:
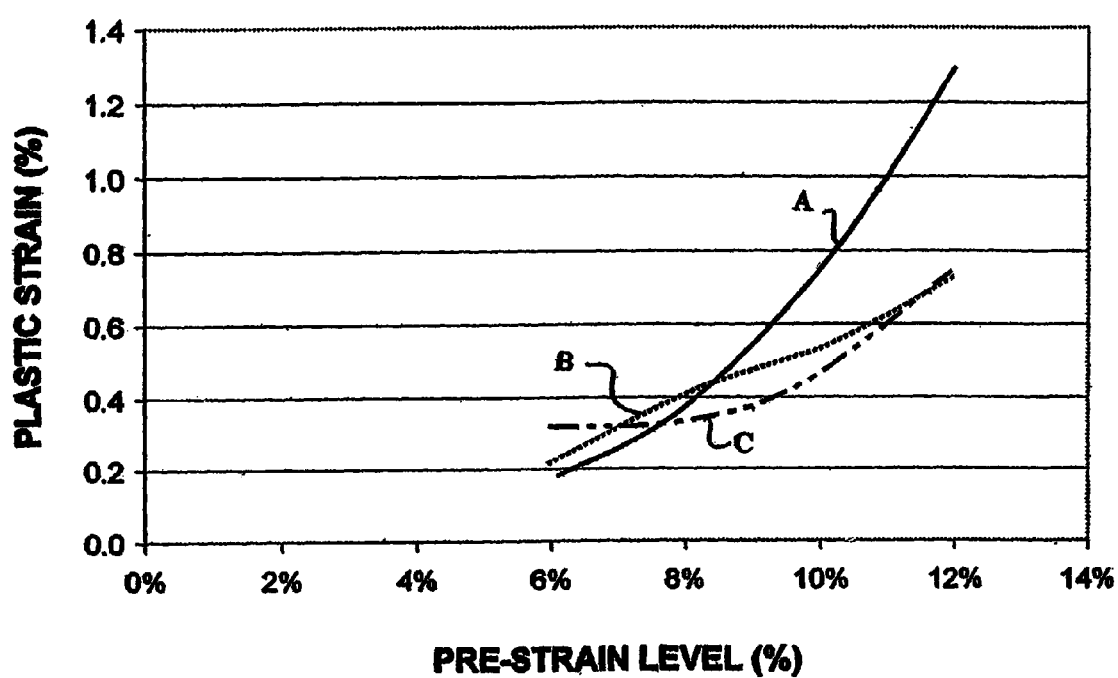
FIG. 5 shows a graph of the non-recoverable strain achieved in nitinol wire when subjected to various methods of tensile pre-straining.

FIG. 5 shows a plot of non-recoverable tensile strain as a function of tensile pre-strain level for the various controlled pre-straining procedures described in FIGS. 2-4. Curve A describes samples subjected to tensile pre-strain at 37° C. and then unloaded at 37° C. (as shown in FIG. 2). Curve B describes samples subjected to tensile pre-strain at −30° C., unloaded at −30° C. and then heated to 37° C. (as shown in FIG. 3). Curve C describes samples subjected to pre-strain at −30° C. and then heated to 37° C. in the pre-strained condition, and subsequently unloaded at 37° C. (as shown in FIG. 4). This type of plot, in conjunction with analytical procedures such as finite element analysis, can be utilized to develop an appropriate temperature, controlled pre-straining process designed to induce non-recoverable tensile strain levels greater than about 0.20% at fatigue-critical locations of a shape-set nitinol structure.

Additional techniques may be utilized to decrease the recoverable strain limit for given pre-strain levels to allow for the introduction of the desired non-recoverable tensile strain at the fatigue-critical locations. These techniques can be incorporated to allow for the introduction of non-recoverable tensile strains at relatively low pre-strain levels (less than 6% to 8% pre-strain). Such techniques include but are not limited to, chemical compositional alloy modifications, thermal and mechanical process history modifications, surface modification techniques such as laser surface treatments, or the like.

Figure 6:
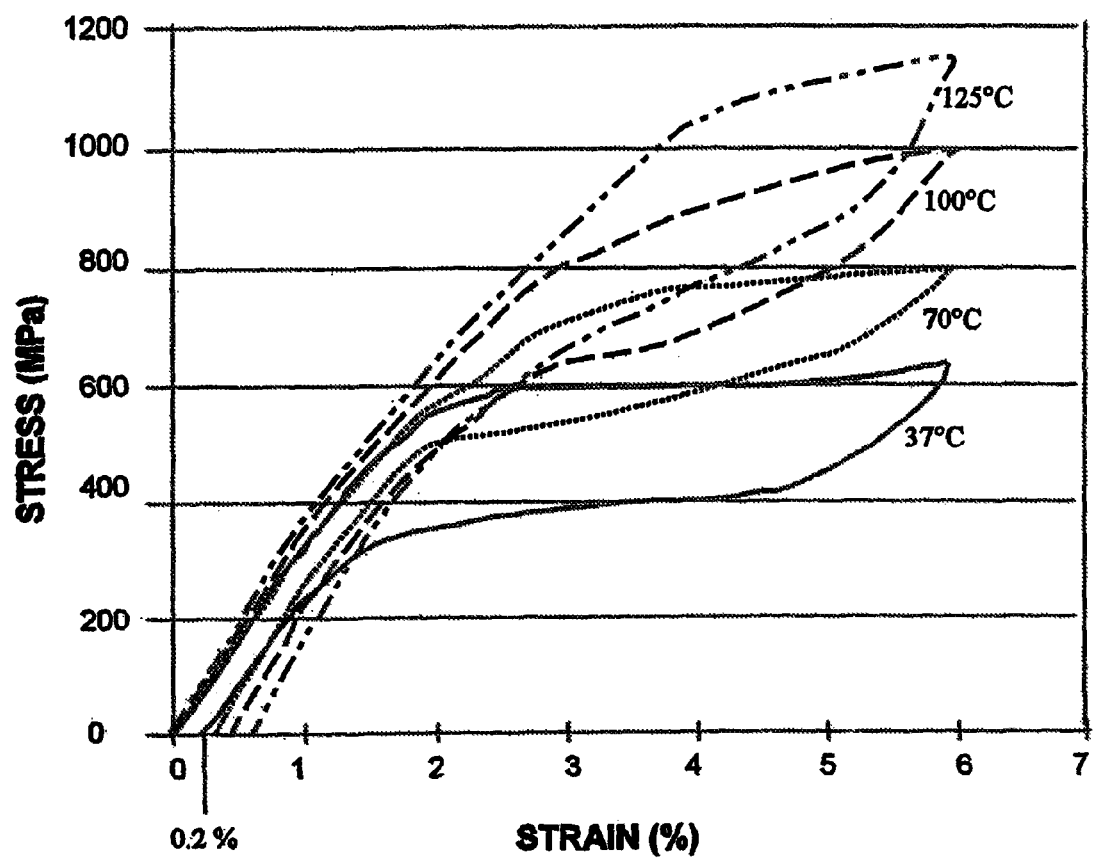
FIG. 6 shows stress-strain curves for nitinol wires subjected to tensile pre-straining treatments at various elevated temperatures.

FIG. 6 shows a family of stress-strain curves for nitinol wire samples loaded in tension to 6% pre-strain and unloaded at various temperatures. The resultant non-recoverable tensile strain is shown to increase with increasing temperature. This provides an example of one technique, by using an elevated temperature pre-straining, which can be used to create relatively high (greater than about 0.20%) non-recoverable strains at relatively low pre-strain levels. This type of plot can be used, in conjunction with analytical procedures such as finite element analysis, to develop an appropriate temperature, controlled pre-straining process designed to induce non-recoverable tensile strain levels greater than about 0.20% at fatigue-critical locations of a shape-set nitinol structure. The use of elevated temperature, controlled pre-straining processes can be utilized to induce non-recoverable tensile strain levels greater than about 0.20% at fatigue-critical locations of a shape-set nitinol structure.

Another technique to provide for the induction of significant (greater than about 0.20%) non-recoverable tensile strains at relatively low pre-strain levels includes the use of a composite structure consisting of a superelastic nitinol core material and an outer surface material with limited recoverable strain capability. The outer material may include a nitinol material with an $A_f$ greater than 37° C., preferably a nitinol material with an $A_s$ greater than 37° C. Alternatively, the outer surface material may also be stainless steel, or any other material with a lower recoverable strain limit than the nitinol core material. The use of such a composite material can allow the introduction of significant non-recoverable tensile surface strains at relatively low pre-strain levels. The induction of non-recoverable tensile surface strains greater than about 0.20% at of near the surface may be introduced by pre-straining the material by bending pre-straining, torsional pre-straining, or a combination of complex pre-strain loading conditions.

The process of inducing compressive residual surface stresses by the pre-straining operations described herein may also produce a concomitant surface region which is subjected to compressive strains, occurring on the opposite surface region of the targeted region subjected to tension, during the pre-straining operation. The compressive strains introduced on the regions opposite the targeted regions may also exceed the recoverable strain limit of the material, resulting in an undesirable residual state of tension at these regions which may result in reduced fatigue life.

FIG. 1C shows the test specimen in a relaxed condition, wherein apex 15 contains no significant residual stresses. Following controlled pre-straining caused by moving pins 11 and 13 closer together, the outer radius of apex 15 of the specimen as shown in FIG. 1C will be in the state of residual compression stress while the inner radius will be in the state of residual tensile stress. This method of pre-straining is thus desired when the critical fatigue location is the outer radius of apex 15. Alternatively, if the fatigue-critical location is the inner radius of apex 15, pre-straining is accomplished by moving pins 11 and 13 further apart. In service, the fatigue-critical location is one that has been previously pre-strained in tension, thus inducing residual compressive stress at that fatigue-critical location.

The end result of the pre-straining operation disclosed in this invention is the improvement in fatigue performance at targeted regions of the medical device structure, thus resulting in a more fatigue resistant device. This operation can thus be applied to specific medical device structure regions where service fatigue loading is most severe and improved fatigue performance is desired, or over the entire surface region of the structure.

In another aspect of the present invention, it is noted that it is not uncommon for nitinol articles including implantable medical articles to be subjected to surface modification by various methods such as electropolishing and shot peening. These methods are known to reduce any non-recoverable strain at the surface of these articles. Consequently, it is appropriate that any desired surface modification is performed prior to the controlled pre-straining operations as taught by the method of the present invention.

Example 1

Axial fatigue tests were conducted using superelastic nitinol wire samples subjected to different tensile pre-strain conditions. The nitinol wire (Fort Wayne Metals, Fort Wayne, Ind., nominal diameter 0.305 mm) utilized for these tests was electropolished to a diameter of 0.300 mm and heat treated in air to obtain a straight configuration and to impart superelastic behavior at 37° C. ($A_f$<37° C.) with a permanent set of less than 0.20% when loaded to 6% strain and unloaded at 37° C.

An Instron servohydraulic test machine (Canton, Mass., model no. 8841) was used for the axial fatigue testing. The testing was performed in an air thermal chamber set at 37° C. (+/−1° C.). Wavemaker software (Fast Track 2, Wavemaker Editor/Runtime, version 7.0.0, provided by Instron) was used to generate and execute the axial fatigue tests using a displacement controlled sine waveform. Test specimen gauge length was 100 mm, held with flat-faced grips (Instron PN 2716-016). Five specimens were pulled to 104 mm length (4% mean strain), and cycled ±0.5 mm (0.5% alternating strain) at cyclic frequencies until failure by fracture, as shown in Table 1. Three additional specimens were pulled to 108 mm length (8% pre-strain), released to 104 mm length (4% mean strain), and cycled ±0.5 mm (0.5% alternating strain), at a cyclic frequency of 12 Hz until fracture (Table 2). An additional three specimens were pulled to 106 mm length (6% pre-strain), released to 104 mm length (4% mean strain), and cycled ±0.5 mm (0.5% alternating strain), at a cyclic frequency of 12 Hz until fracture (Table 3).

Test results as presented in Tables 1-3 show an increase in fatigue life with an increase in pre-strain level.

TABLE 1

No pre-strain, 4% mean strain, 0.5% alternating strain

| Specimen | cyclic frequency | CTF |
| --- | --- | --- |
| 1 | 8 Hz | 3,852 |
| 2 | 8 Hz | 2,998 |
| 3 | 15 Hz | 3,383 |
| 4 | 12 Hz | 3,868 |
| 5 | 12 Hz | 3,988 | mean CTF: 3618 cycles

TABLE 2

8% pre-strain, 4% mean strain, 0.5% alternating strain

| Specimen | cyclic frequency | CTF |
| --- | --- | --- |
| 6 | 12 Hz | 9,266 |
| 7 | 12 Hz | 9,779 |
| 8 | 12 Hz | 9,533 | mean CTF: 9526 cycles

TABLE 3

6% pre-strain, 4% mean strain, 0.5% alternating strain

| Specimen | cyclic frequency | CTF |
| --- | --- | --- |
| 9 | 12 Hz | 6,185 |
| 10 | 12 Hz | 7,520 |
| 11 | 12 Hz | 7,541 | mean CTF: 7082 cycles

Figure 7:
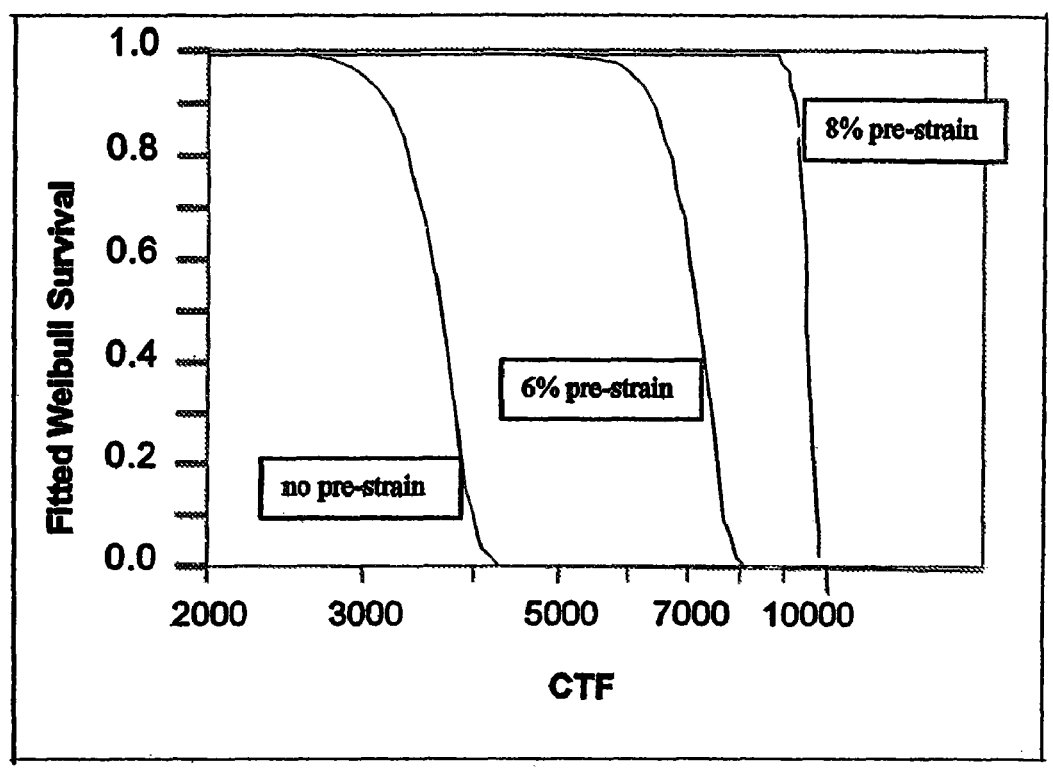
FIG. 7 shows a fitted Weibull fatigue survivability plot for a group of nitinol wire samples provided with tensile pre-straining treatment in accordance with embodiments of the present invention, compared to a non pre-strained control group when both groups were subjected to an axial fatigue test.

The axial fatigue test results are summarized in FIG. 7, showing a fitted Weibull distribution fatigue survival plot comparing the fatigue lives for different groups of nitinol wire samples (plotted as proportion of survivors within each group versus number of cycles to failure, or CTF).

Example 2

Flexural fatigue tests were conducted using superelastic nitinol wire (Fort Wayne Metals, Fort Wayne, Ind., nominal diameter 0.323 mm) samples subjected to different tensile pre-strain conditions. The nitinol wire used for these tests was electropolished to a diameter of 0.321 mm.

Thirty wire test specimens were formed into the shape described in FIG. 1C, by winding the wire around the 0.79 mm diameter stainless steel pins 11, 12 and 13 of the heat treatment fixture, as shown in FIG. 1C. All test specimens were heat treated in air while on the fixture to set the test sample geometry configuration and to to impart superelastic behavior at 37° C. ($A_f$<37° C.) with a permanent set of less than 0.20% when loaded to 6% strain and unloaded at 37° C. Dimension "A" between pins 11 and 13 (center-to-center) was 13.72 mm, while dimension "B" was half of dimension "A". Dimension "C" was 5.08 mm. The support loops 14 at the ends of each sample 10 were of an inside diameter that conforms to the diameter of pins 11 and 13. The apex 15 of each test specimen 10 was formed to a radius (at the inside radius of the apex bend) that conformed to the diameter of pin 12.

Prepared test specimens were divided into three separate groups (10 samples per group): a control group (Group 1: no pre-strain), a room temperature pre-strain group (Group 2), and a cold pre-strain group (Group 3). Each sample from Group 2 was pre-strained by placing the sample eyelet support loops (14) onto the same pin (11) to pre-strain the test sample apex (15) at room temperature. The test specimens were kept at this condition for 2 hours at room temperature and then removed. Group 3 samples were placed into a bath mixture of dry ice and 100% isopropyl alcohol, with a submersed thermocouple to monitor bath temperature. The samples were then pre-strained while submersed in the bath, following the same pre-strain procedure described for Group 2. The bath temperature ranged from −34° C. to −14° C. during the pre-straining procedure. The samples were removed from the bath while in the constrained condition and placed in room temperature air for 2 hours prior to removal of the pre-strain constraint. Group 1 was not pre-strained, and served as control samples for the subsequent fatigue tests. The maximum principle tensile pre-strain level at the fatigue-critical location (outside radius surface of the apex) was calculated to be approximately 8.5%. This maximum principle pre-strain level was calculated by applying standard engineering mechanics formulas (straight and curved beam deflection equations, from "Roark's Formulas for Stress & Strain," $6^{th}$ edition, McGraw Hill, New York, N.Y.) to the specimen geometry.

Fatigue tests were conducted using a fatigue tester designed and built for the purpose of conducting cyclic, deflection controlled, fatigue testing of apical wire samples of the previously described geometry. The tester is designed to accommodate up to forty test samples. Wire fatigue test samples were loaded onto the fatigue test apparatus by placing the test sample support loops onto 0.79 mm diameter stainless steel pins of the fatigue tester. The tester was set to alternate test pin deflections from 9.20 mm and 10.16 mm (i.e., dimension "A" of FIG. 1C alternated between 9.20 mm and 10.16 mm). These deflections were selected to achieve a maximum principle mean tensile strain of 2.5% and an alternating strain of 0.3% at the outside radius of the test specimen apex. The maximum principle strains for these deflections was calculated by applying standard engineering mechanics formulas (straight and curved beam deflection equations, from "Roark's Formulas for Stress & Strain," $6^{th}$ edition, McGraw Hill, New York, N.Y.) to the specimen geometry.

These deflections were set-up using a telescoping dial depth gage and gage blocks. All 30 specimens were mounted on the tester, with test and control samples being placed alternately along the test fixture. The fatigue testing was performed in a 37±1° C. water bath and at a cyclic frequency of approximately 18 Hz.

Figure 8:
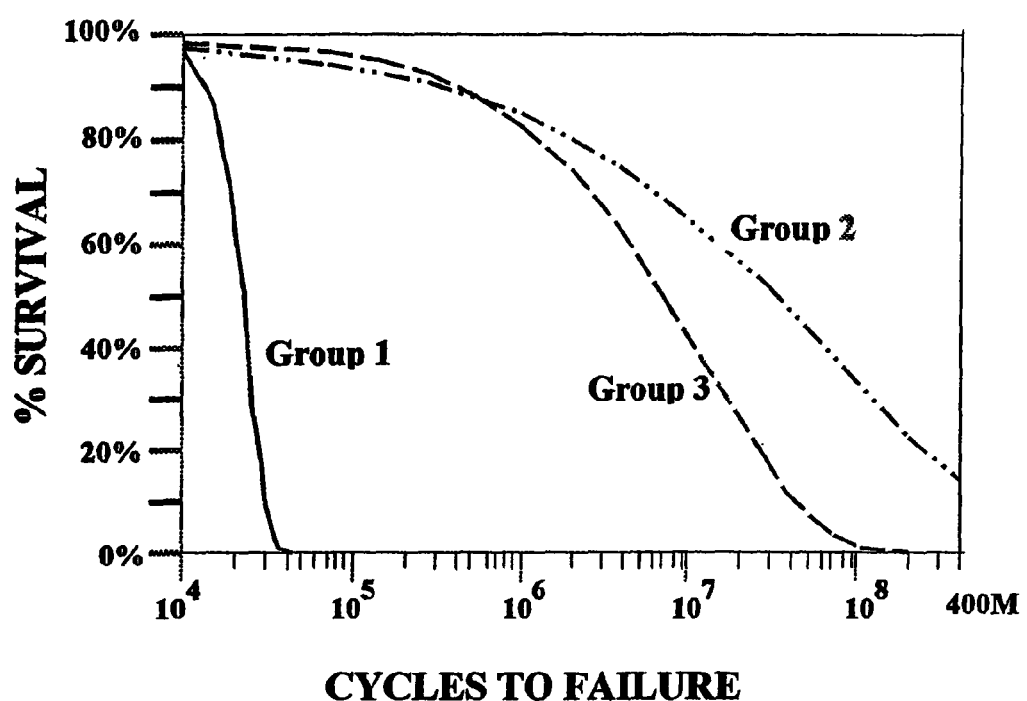
FIG. 8 shows a fitted Weibull fatigue survivability plot for a group of nitinol wire samples provided with bending pre-straining treatment in accordance with embodiments of the present invention, compared to the non pre-strained control group when both groups were subjected to a flexural fatigue test.

The flexural fatigue test results are summarized in FIG. 8, showing a fitted Weibull distribution fatigue survival plot comparing the fatigue lives for different groups of nitinol wire samples (plotted as proportion of survivors within each group versus number of cycles to failure by fracture at the apex, or CTF). Data are presented in Tables 4-6 for Groups 1-3 respectively. Various specimens from Groups 2 and 3 survived the 40 million cycle length of the tests as noted. The fatigue test results demonstrate an improvement of approximately three orders of magnitude in the mean fatigue lives for the pre-strained sample groups. This example demonstrates the significant improvement in the fatigue performance of nitinol (particularly nitinol wire) when subjected to a pre-straining treatment.

TABLE 4

Controls, No Pre-Strain

| Specimen | CTF |
|---|---|
| 1 | 13,002 |
| 2 | 17,004 |
| 3 | 20,000 |
| 4 | 20,000 |
| 5 | 23,006 |
| 6 | 24,002 |
| 7 | 24,002 |
| 8 | 24,002 |
| 9 | 29,006 |
| 10 | 37,002 |

TABLE 5

Room Temperature Pre-Strain

| Specimen | CTF |
|---|---|
| 1 | 125,055 |
| 2 | 1,300,000 |
| 3 | 4,148,832 |
| 4 | 4,246,188 |
| 5 | 12,408,376 |
| 6 | 40,000,000+ |
| 7 | 40,000,000+ |
| 8 | 40,000,000+ |
| 9 | 40,000,000+ |
| 10 | 40,000,000+ |

TABLE 6

Cold Pre-Strain

| Specimen | CTF |
|---|---|
| 1 | 755,022 |
| 2 | 2,229,536 |
| 3 | 2,399,999 |
| 4 | 2,481,166 |
| 5 | 2,817,037 |
| 6 | 7,723,746 |
| 7 | 8,242,257 |
| 8 | 9,278,477 |
| 9 | 40,000,000+ |
| 10 | 40,000,000+ |

While the principles of the invention have been made clear in the illustrative embodiments set forth herein, it will be obvious to those skilled in the art to make various modifications to the structure, arrangement, proportion, elements, materials and components used in the practice of the invention. To the extent that these various modifications do not depart from the spirit and scope of the appended claims, they are intended to be encompassed therein.

We claim:

1. A self-expanding stent comprising a frame formed from nitinol exhibiting superelastic behavior at body temperature, the frame being configured to self-expand from a constrained delivery profile to an expanded operative profile, wherein the frame is pre-strained by the application of a pre-straining bending force to an extent that selectively induces at least about 8.0% tensile strain at or near only a surface of at least one selected location on the frame during circumferential compaction of the frame to a smaller size, wherein following release of the pre-straining force, the frame returns to, or near to, its geometry prior to the application of the pre-straining force.

2. A self-expanding stent according to claim 1 wherein the pre-straining results in at least about 8.5% tensile strain.

3. A self-expanding stent according to claim 1 wherein the stent is a stent-graft.

4. A self-expanding stent according to claim 2 wherein the stent is a stent-graft.

5. A self-expanding filter device comprising a frame formed from nitinol exhibiting superelastic behavior at body temperature, the frame being configured to self-expand from a constrained delivery profile to an expanded operative profile, wherein the frame is pre-strained by the application of a pre-straining bending force to an extent that selectively induces at least about 8.0% tensile strain at or near only a surface of at least one selected location on the frame during circumferential compaction of the frame to a smaller size, wherein following release of the pre-straining force, the frame returns to, or near to, its geometry prior to the application of the pre-straining force.

6. A self-expanding filter device according to claim 5 wherein the pre-straining results in at least about 8.5% tensile strain.

* * * * *